US006975901B2

United States Patent
Philip

(10) Patent No.: US 6,975,901 B2
(45) Date of Patent: Dec. 13, 2005

(54) ANESTHETIC-STATE DETERMING

(75) Inventor: James H. Philip, Chestnut Hill, MA (US)

(73) Assignee: The Brigham and Women's Hopital, Inc., Boston, MA (US)

( * ) Notice: Subject to any disclaimer, the term of this patent is extended or adjusted under 35 U.S.C. 154(b) by 1 day.

(21) Appl. No.: 10/655,673

(22) Filed: Sep. 5, 2003

(65) Prior Publication Data
US 2004/0167425 A1 Aug. 26, 2004

Related U.S. Application Data

(60) Provisional application No. 60/408,564, filed on Sep. 6, 2002.

(51) Int. Cl.$^7$ .............................................. A61B 5/00
(52) U.S. Cl. ..................................... 600/544; 600/545
(58) Field of Search .................................... 600/544–5

(56) References Cited

U.S. PATENT DOCUMENTS

| | | | | |
|---|---|---|---|---|
| 3,901,215 A | | 8/1975 | John ........................ | 128/2.1 B |
| 4,557,270 A | * | 12/1985 | John .......................... | 600/544 |
| 5,113,870 A | * | 5/1992 | Rossenfeld ................ | 600/544 |
| 5,195,531 A | * | 3/1993 | Bennett ...................... | 600/546 |
| 5,694,939 A | * | 12/1997 | Cowings ..................... | 600/484 |
| 6,500,128 B2 | * | 12/2002 | Marino ........................ | 600/554 |

OTHER PUBLICATIONS

International Search Report for PCT/US03/27904, mailed Jun. 1, 2005.

* cited by examiner

Primary Examiner—Robert L. Nasser
(74) Attorney, Agent, or Firm—Ivor R. Elrifi; Shane H. Hunter; Mintz, Levin, Cohn, Ferris, Glovsky and Popeo, P.C.

(57) ABSTRACT

A system for determining anesthetic state of a subject includes a brain monitor configured to measure at least one parameter of brain activity of the subject and to provide at least one brain monitor output signal indicative of the measured at least one parameter, a stimulator configured to apply a non-surgical stimulus perturbation to the subject and to provide at least one stimulus output signal indicative of timing and intensity of non-surgical stimuli applied to the subject, an analyzer coupled to the brain monitor and the stimulator and configured to receive the at least one brain monitor output signal and the at least one stimulus output signal, to determine a stimulus difference between the non-surgical stimulus intensity in the absence of the perturbation and in the presence of the perturbation, to determine a monitor difference between the a first value of the at least one parameter in the absence of the perturbation and a second value of the at least one parameter in the presence of the perturbation, to make a comparison of the stimulus difference and the monitor difference, and to provide an indication of the comparison, and a display coupled to the analyzer and configured to receive the indication of the comparison, and in response to receiving the indication of the comparison to provide at least one of an audible sound and a visual image indicative of the indication of the comparison.

14 Claims, 3 Drawing Sheets

ANESTHETIC-STATE DETERMING

CROSS-REFERENCE TO RELATED ACTIONS

This application claims the benefit of U.S. Provisional Application No. 60/408,564 filed Sep. 6, 2002.

FIELD OF THE INVENTION

The invention relates to anesthetizing patients and more particularly to detecting anesthetic states of patients.

BACKGROUND OF THE INVENTION

Patients are often anesthetized before receiving medical treatment. For example, patients are anesthetized before surgery, using either a local anesthetic or a general anesthetic, especially for major operations.

Anesthesiologists typically monitor bodily functions to determine whether a patient is properly anesthetized for the procedure that the patient is to receive. For example, the anesthesiologist may monitor the patient's blood pressure, heart rate, amount of sweating, and/or pupil size to determine whether the patient is sufficiently anesthetized for the procedure at hand, while not being too heavily anesthetized. If the anesthesiologist is mistaken about whether the patient is appropriately anesthetized, e.g., if the patient is insufficiently anesthetized for the current procedure, then several undesirable consequences may result. The patient's bodily functions may jump (e.g., blood pressure and heart rate increase) and/or other reactions may occur such as the patient's muscles contracting that may cause the patient to move. This latter consequence may be especially undesirable if the patient is being incised at the time. Further, if not properly anesthetized, the patient may even wake up, potentially making for a particularly frightening if not painful experience for the patient.

SUMMARY OF THE INVENTION

In general, in an aspect, the invention provides a system for determining anesthetic state of a subject, the system including a brain monitor configured to measure at least one parameter of brain activity of the subject and to provide at least one brain monitor output signal indicative of the measured at least one parameter, a stimulator configured to apply a non-surgical stimulus perturbation to the subject and to provide at least one stimulus output signal indicative of timing and intensity of non-surgical stimuli applied to the subject, an analyzer coupled to the brain monitor and the stimulator and configured to receive the at least one brain monitor output signal and the at least one stimulus output signal, to determine a stimulus difference between the non-surgical stimulus intensity in the absence of the perturbation and in the presence of the perturbation, to determine a monitor difference between the a first value of the at least one parameter in the absence of the perturbation and a second value of the at least one parameter in the presence of the perturbation, to make a comparison of the stimulus difference and the monitor difference, and to provide an indication of the comparison, and a display coupled to the analyzer and configured to receive the indication of the comparison, and in response to receiving the indication of the comparison to provide at least one of an audible sound and a visual image indicative of the indication of the comparison.

Implementations of the invention may include one or more of the following features. The system further includes a housing containing at least the brain monitor and the analyzer. The housing further contains at least the display. The comparison is a ratio of the stimulus difference and the monitor difference.

In general, in another aspect, the invention provides a monitor for determining anesthetic state of a subject, the monitor being for use with a stimulator for applying a non-surgical perturbation stimulus to a patient and providing indicia of intensity of the applied stimulus. The monitor includes a sensor adapted to couple to the patient and to sense at least one bodily parameter that is at least partially indicative of anesthetic state, and to provide a sensor output indicative of the sensed at least one bodily parameter, an input configured to couple to the stimulator to receive the indicia of timing and intensity of the applied stimulus, and an analyzer coupled to the sensor and the input and configured to process the sensor output and the indicia of intensity of the applied stimulus to determine a comparison between (1) the sensor output without the perturbation and the sensor output when the subject responds to the perturbation and (2) the applied stimulus during a time other than when the perturbation is applied and the applied stimulus during application of the perturbation.

Implementations of the invention may include one or more of the following features. The sensor is configured to sense brain activity. The comparison is a ratio.

In general, in another aspect, the invention provides a method of determining anesthetic state of a patient prior to performing a procedure on the patient, the method including sensing at least one bodily parameter of the patient that is at least partially indicative of anesthetic state, providing a sensed signal indicative of the sensed at least one bodily parameter, applying a stimulus perturbation to the patient, the stimulus perturbation being different from the procedure, analyzing the sensed signal from a first time when the patient is reacting to the stimulus perturbation and from a second time other than the when the patient is reacting to the stimulus perturbation, and analyzing a first intensity of the stimulus perturbation and a second intensity of a stimulus, if any, provided to the patient during the second time.

Implementations of the invention may include one or more of the following features. Analyzing the sensed signal includes determining a difference between the sensed signal at the first and second times. Analyzing the first and second intensities includes determining a difference between the first and second intensities. The method further includes comparing the difference between the sensed signal and the difference between the first and second intensities. The comparing includes determining a ratio of the differences. The at least one bodily parameter is indicative of brain activity.

Various aspects of the invention may provide one or more of the following advantages. States of anesthesia of patients can be objectively determined before procedures are performed on the patients. Existing patient monitors may be adapted to indicate levels of anesthesia of patients. Expected reactions to surgical procedures by patients can be determined without, and before, subjecting the patient to the actual procedure. Expected reactions can be determined for a variety of surgical procedures having different severities of impact upon patients.

These and other advantages of the invention, along with the invention itself, will be more fully understood after a review of the following figures, detailed description, and claims.

DETAILED DESCRIPTION OF PREFERRED EMBODIMENTS

Figure 1:
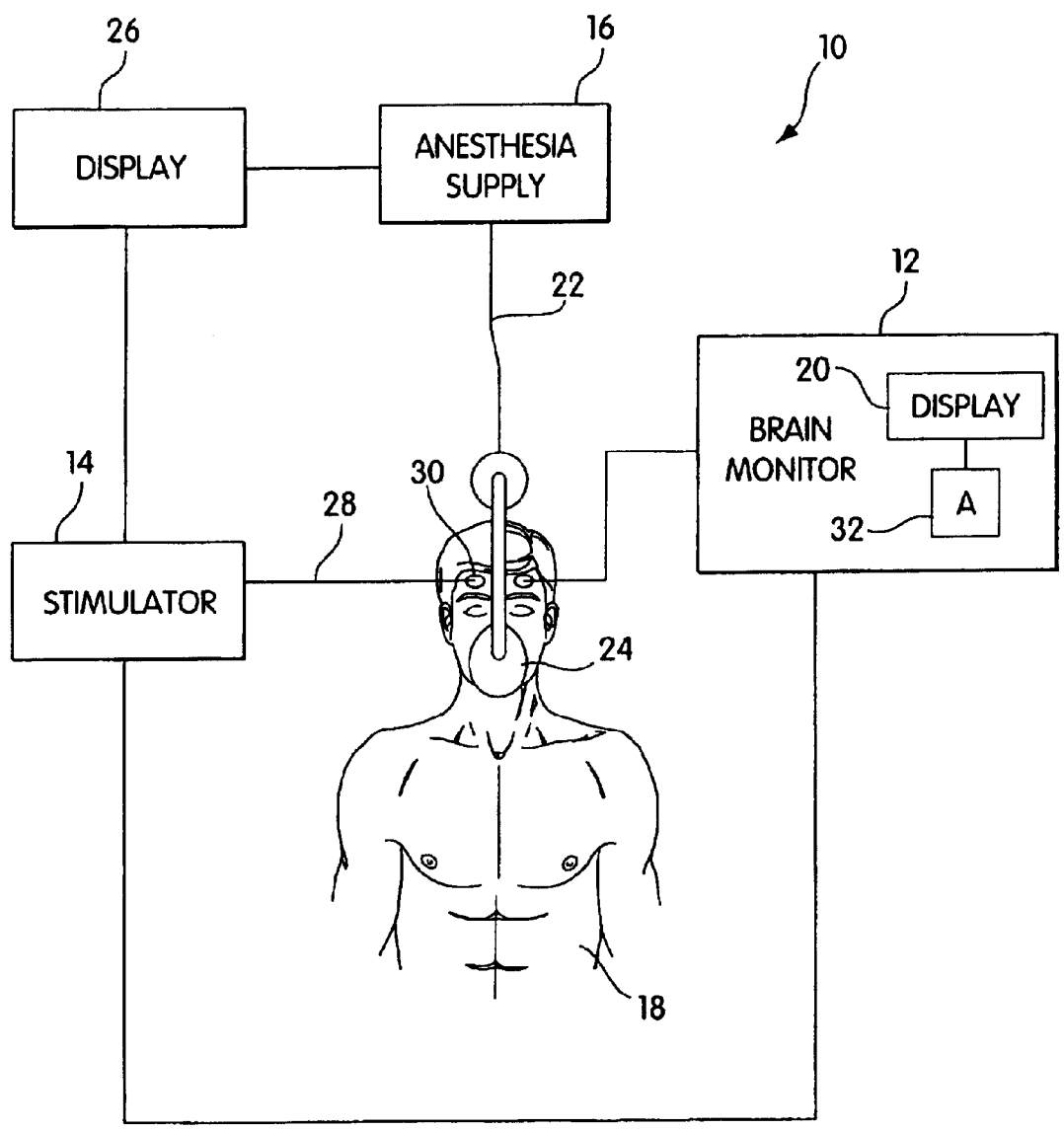
FIG. 1 is a schematic diagram of a system for determining anesthetic state of a patient.

Referring to FIG. 1, a system 10 includes a brain monitor 12, a stimulator 14, and an anesthesia supply 16. The system 10 is configured to provide one or more stimuli to a patient 18 and to monitor the patient's reaction(s) to those stimuli.

The anesthesia supply 16 may also be an off-the-shelf item for delivering anesthesia to the patient 18. The supply 16 is configured to provide anesthesia and oxygen (and other gases as appropriate) to the patient 18 through a flexible tube 22 and a mask 24. The supply 16 can be any current or future such supply and preferably provides indicia to a display 26 of amounts of materials provided to the patient 18. The supply 16 may also, or instead of through the tube and mask 24, supply anesthesia intravenously through an IV line 23 to the patient 18. Other techniques for supplying anesthesia to the patient 18 are also acceptable.

The stimulator 14 is configured to provide a stimulus perturbation to the patient 18 that will provide information as to the anesthetic state of the patient 18. The stimulus perturbation is preferably a purposeful stimulus that is different than the actual procedure, although the stimulus may be similar in kind and/or intensity to the procedure, that the patient 18 is to undergo. The procedure that the patient is to undergo may be part of a larger procedure that the patient is currently undergoing. As shown, the stimulator 14 is configured to send an electrical stimulus to the patient 18 through a line 28 and an electrically-conductive pad 30. The electrical stimulus can be provided in varying intensities as selected through one or more controls of the stimulator 14. The stimuli can be changed as desired/needed (e.g., in accordance with procedure and/or results of prior stimuli and analysis). Also, other forms of stimuli are acceptable such as a thermal stimulus, e.g., using a laser. Further, other acceptable stimuli include a mechanical stimulus, e.g., a pinch, a prick, a sharp or blunt impact, etc. using a mechanical stimulator apparatus configured to provide the desired mechanical stimulus. Additionally, more than one stimuli, including different types of stimuli, may be applied, e.g., concurrently. Preferably, however, the stimulator 14 provides a single form of stimulus, to a single portion of the patient 18, of a desired intensity. The stimulator 14 may provide a steady-state stimulus, e.g., a low-intensity stimulus (that may be zero, i.e., no stimulus), with the perturbation being a change (e.g., a sudden, significant increase) in intensity of the stimulus. The stimulator 14 is coupled to the display 26 and configured to supply signals indicating intensity of the stimulus to the display 26. Further, the stimulator 14 is coupled to the monitor 12 and configured to supply output signals to the monitor 12 indicating amounts of stimuli provided to the patient 18.

The monitor 12 is configured to provide one or more indicia of the state of anesthesia induced by the supply 16 including indicia of the patient's response to the stimulus from the stimulator 14. The monitor 12 may be an off-the-shelf monitor modified to provide the desired functionality. For example, the brain monitor 12 may be a BIS monitor made by Aspect Medical Systems, Inc. of Natick, Mass., or a Patient State Analyzer (PSA) 4000 made by Physiometrix, Inc. of Billerica, Mass. The monitor 12 provides indicia of brain activity such as an electroencephalogram (EEG) and/or an electromyograph (EMG), or measures extracted or derived from the EEG and/or EMG. As shown, the monitor 12 includes a display 20 for displaying monitored data, e.g., an electroencephalograph, and/or processed/computed data indicative of a change in the brain-activity indicia or measures extracted or derived from such measures. The monitor 12, however, may not have its own display and may be connected to a separate display (e.g., the display 26). The monitor 12 is configured to detect various physiological parameters of the patient's brain and to provide indicia of these parameters, and computed anesthetic-state indicia as discussed below, to the display 20.

The monitor 12 includes custom software that includes instructions for execution by a computer processor of the monitor 12 to perform operations to indicate anesthetic state. Anesthetic state is derived from the signals output by the stimulator 14 in combination with monitored patient information. The stimulator output signals indicate the intensity of the stimulus provided to the patient 18 and the monitor 12 can effect changes in the stimulus intensity (e.g., from zero stimulus to some level of stimulus, or between non-zero levels of stimulus). The monitor 12 can also determine differences between monitor value outputs. For example, if the monitor 12 displays an awareness value of 0 indicating that the patient 18 is asleep (as determined by processing monitored information), and 100 indicating that the patient 18 is wide awake, the monitor 12 can determine deltas between the awareness values before and after stimulus introduction, or before and after a change in stimulation, by the stimulator 14. The monitor 12 can normalize the detected patient response to the stimulus by the stimulus change value according to:

$$\frac{\text{change in monitor value}}{\text{change in stimulus intensity}} = \text{anesthetic-state value} \quad (1)$$

The stimulus and response may be transient, with the changes being the differences between the respective values before (or after) the stimulus and at peak stimulation/response, respectively. Differences can be, e.g., results of subtractions, ratios, deconvolutions, or other measures of relationship. The anesthetic-state value resulting from equation (1) provides an indication of the level of anesthesia of the patient 18, and thus how prepared the patient 18 is, at least from an anesthesia perspective, for a procedure.

The anesthetic-state value provided by the monitor 12 can be used by an anesthetist or other person to evaluate the preparedness of the patient 18 for the procedure that the patient 18 is to undergo. Preferably, the anesthetic-state value will be at or below a threshold value, indicating that the patient 18 is adequately anesthetized. The threshold value, and/or the stimulus (e.g., type and/or intensity) may be dependent upon the particular procedure to be performed. Further, the change in monitor value may be non-linear with respect to the change in stimulus intensity. Thus, a non-linear factor may be applied to (e.g., multiplied by) the anesthetic-state value to account for this fact, and/or the threshold value may be dependent upon the change in stimulus intensity. This non-linearity may be derived from, e.g., experimental data. Determining the non-linearity may help allow a small stimulus to be applied to the patient 18 while providing reliable information as to whether the patient 18 is sufficiently anesthetized.

The monitor 12 itself may provide an indication of the patient's preparedness for a procedure. The monitor 12 may include an analyzer 32, e.g., further software code configured to analyze the anesthetic-state value. The analyzer 32 can compare the anesthetic-state value against the threshold and provide a signal to the display 20 regarding the comparison. For example, the signal to the display 20 could cause the display 20 to indicate "Ready" or the like if the anesthetic-state value is at or below the threshold value, and to indicate "NOT Ready" or the like otherwise. The analyzer 32 can receive an indication of the threshold value or of the procedure to be undergone in order to determine the appropriate threshold, e.g., by searching a look-up table of procedures and associated thresholds. The analyzer 32 can further receive an indication of the stimulus intensity change to determine an appropriate adjustment for the anesthetic-state value, e.g., using a look-up table of stimulus change intensities and associated anesthetic-state value adjustments.

Figure 2:
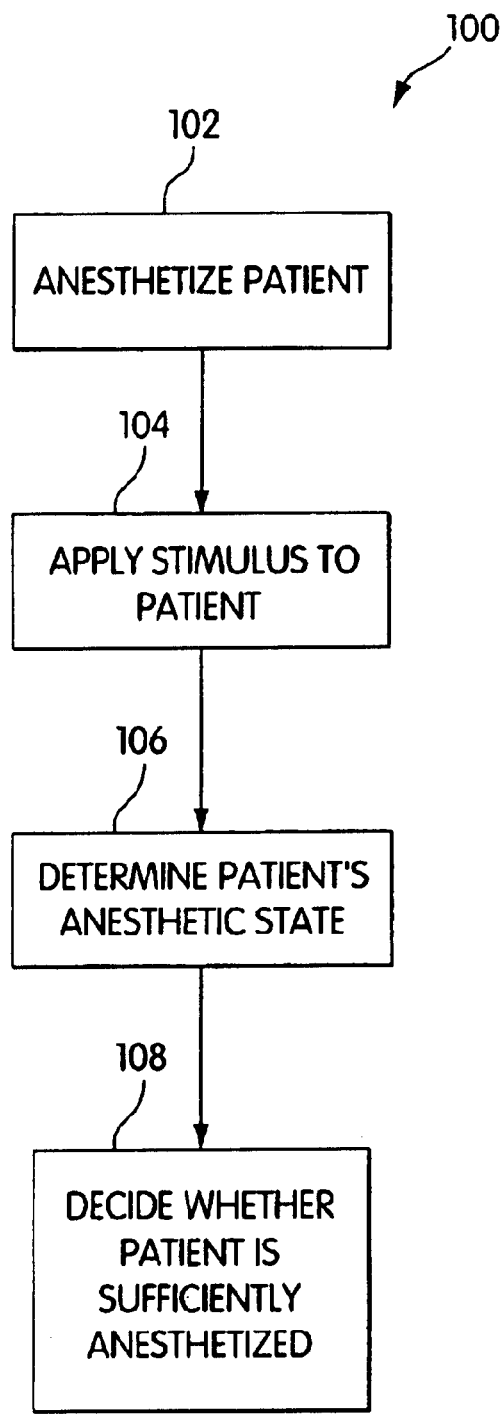
FIG. 2 is a block flow diagram of a process of determining anesthetic state using the system of FIG. 1.

In operation, referring to FIG. 2, with further reference to FIG. 1, a process 100 of using the system 10 to determine the patient's state of anesthetization includes the stages shown. The process 100, however, is exemplary only and not limiting. The process 100 can be altered, e.g., by having stages added, removed, or rearranged. The process 100 may be implemented before or during a procedure underdone by the patient.

At stage 102, the patient 18 is anesthetized. An anesthesiologist (or intensives or other appropriate person) applies anesthesia to the patient 18 using the anesthesia supply 16. The amount and type of anesthesia applied will vary depending upon the patient 18 (e.g., physical characteristics such as age and weight) and upon the procedure that the patient 18 is to undergo that has not yet started or that is part of a larger procedure that the patient is currently experiencing.

At stage 104, a stimulus is applied to the patient 18 and the patient's response is monitored. The stimulator 14 is actuated to apply the stimulus to the patient 18. The stimulator 14 outputs signals corresponding to the stimulus as inputs to the monitor 12 for use in determining the anesthetic-state value. For use in determining the anesthetic-state value, the monitor 12 further uses physiological parameters of the patient 18 including the patient's response to the stimulus as detected/measured by the monitor 12.

At stage 106, the stimulus and the patient's reaction to the applied stimulus are monitored. The monitor 12 detects/monitors the patient's response and provides at least one indication of the response. The stimulator 14 provides its output signals providing at least one indication of the stimulus applied (e.g., the change in stimulus intensity applied).

At stage 108, the patient's anesthetic state is determined. Values of the stimulator output and the detected/monitored parameters are processed to determine the changes in stimulus and in the monitor's value. These change values are used in equation (1) to derive the anesthetic-state value. This value is displayed on the display 20.

At stage 110, the anesthetic-state value is used to assess the depth of anesthesia of the patient 18 for the applicable procedure. An anesthetist or other appropriate person may analyze the anesthetic-state value and make a judgment based on the procedure to be performed on the patient 18 as to the patient's preparedness. This analysis may be a comparison to a chart of procedures and threshold anesthetic-state values. Alternatively, or additionally, the monitor 12 may provide an indication of the patient's preparedness on the display 20. The monitor 12 can look up the threshold for the applicable procedure in a look-up table, compare the found threshold with the calculated anesthetic-state value, and actuate the display to indicate accordingly. The monitor 12 can actuate the display 20 to indicate "Ready" or the like if the threshold is above the calculated value (i.e., the patient's reaction to the stimulus change is too great) and to indicate "NOT Ready" or the like otherwise (i.e., the patient's reaction to the stimulus change is acceptable). A person making and/or influencing the final determination as to whether to proceed with the procedure may use factors, e.g., indicia on the displays 20, 26, in addition to or instead of the anesthetic-state value, or ready/not ready indication, etc., provided by the analyzer 32.

Figure 3:
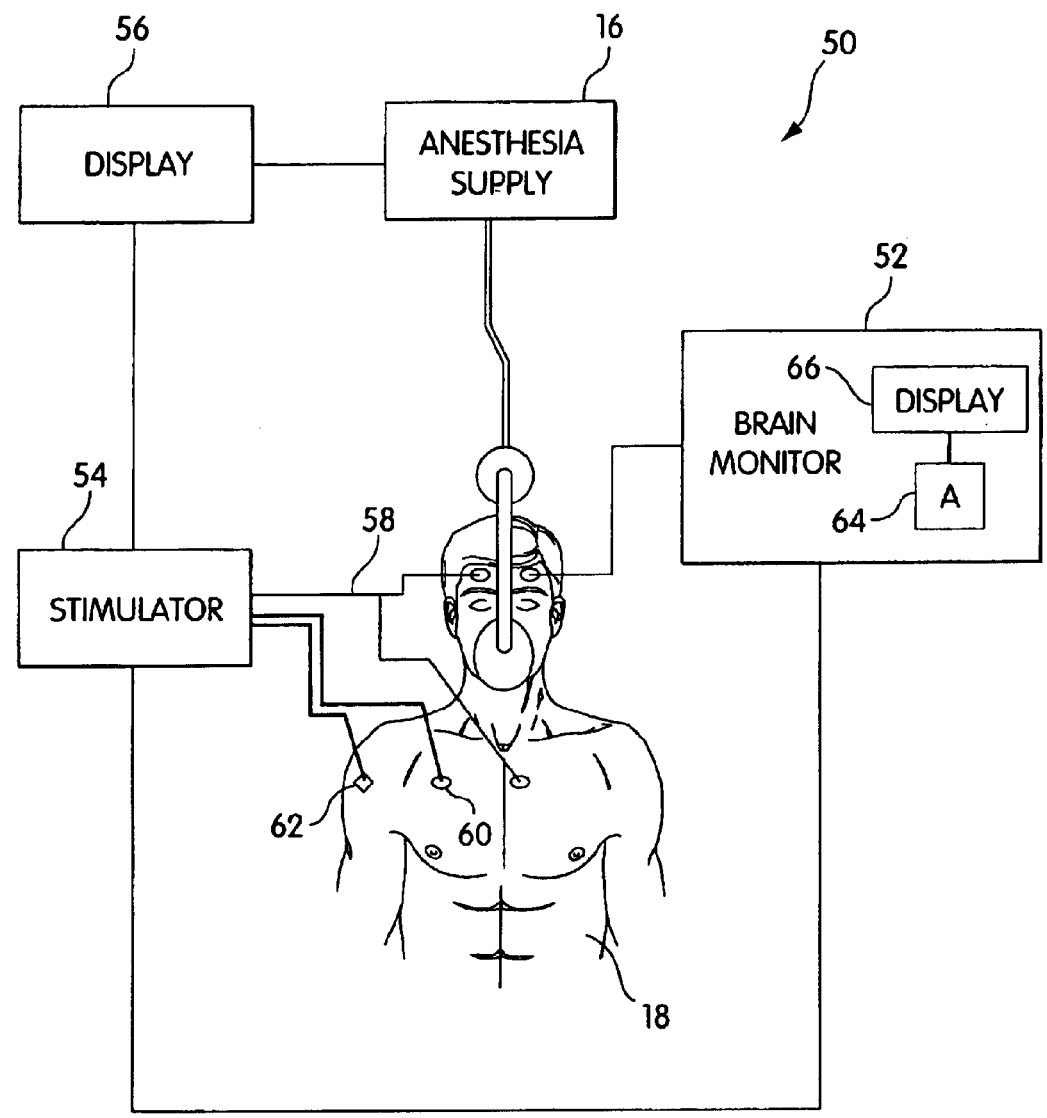
FIG. 3 is a schematic diagram of another system for determining anesthetic state of a patient.

Numerous other configurations of the system 10 are possible and within the scope of the invention and the appended claims. Referring to FIG. 3, a system 50 includes a brain monitor 52, a stimulator 54, and a display 56 for use with the patient 18.

As shown, the stimulator 54 is configured to provide multiple stimuli to the patient 18 in multiple forms. A line 58 from the stimulator 54 for providing electrical stimuli is split and coupled to multiple contact pads attached to the patient 18 to stimulate multiple portions of the patient 18. The stimulator is further connected to a thermal pad 60 for providing thermal stimuli to the patient 18. Further, the stimulator 54 is configured to provide a mechanical stimulus, e.g., a pinch, a prick, a sharp or blunt impact, etc. Using a mechanical stimulator arm 62 configured to provide the desired mechanical stimulus. For example, the arm 62 could include pincers, or a blunt or pointed shaft that is pneumatically or electromagnetically driven to be pushed into contact with the patient 18. The stimulator 54 can be configured to provide electrical and/or thermal stimuli to other portions of the patient 18 than as shown, to provide more stimuli than shown, and/or to provide multiple stimuli of one or more types (e.g., electrical, thermal, mechanical) concurrently. Outputs from the stimulator are conveyed to the display 56 for indicating stimuli levels and to the brain monitor 52 for analysis in conjunction with monitored brain activity of the patient 18 to determine anesthetic state.

An analyzer 64 of the monitor 12 is configured to analyze reactions of the patient 18 to stimuli and changes in stimuli intensities, and to calculate an anesthetic-state value. The anesthetic-state value calculated by the analyzer 64 according to:

$$\frac{\text{change in monitor value}}{\text{aggregate change in stimuli intensities}} = \text{anesthetic-state value} \quad (2)$$

The aggregate change in stimuli intensities is a combination of the changes in intensities associated with the various stimuli applied to the patient 18 by the stimulator 54. The combination may take a variety of forms including, but not limited to, an average or a weighted average. Weights of any of the stimuli may be set to zero to effectively eliminate one or more stimuli from consideration. The analyzer 64 can determine a ready/not ready state based upon a threshold as discussed above, and can cause a display 66 of the monitor 52 to provide indicia of the ready/not ready determination. The analyzer 64 may be a separate unit apart from the monitor 52 and may supply indicia of the anesthetic-state value and/or the ready/not ready state to the display 56.

The brain monitor 52 may be more than one monitor and/or may monitor more than just brain-related parameters. For example, the monitor 52 may include heart-rate monitoring, blood-pressure monitoring, etc. Parameters associated with such monitoring may be used in combination to determine the anesthetic-state value, e.g., by taking an average or weighted average of changes in parameters monitored and normalizing by the aggregate change in stimuli intensities. The various monitored parameters may be used to determine separate anesthetic-state values. These separate values may be processed, e.g., by averaging or weighted-averaging the multiple values.

Further, multiple levels and/or a continuum of anesthetic preparedness may be indicated by the monitors 12, 52 and displayed by the displays 20, 26. Multiple thresholds may be compared to the anesthetic-state value determined according to equations (1) or (2). These comparisons to multiple thresholds can place the anesthetic-state value into one of multiple ranges of anesthetic state (e.g., low anesthetic-state, medium anesthetic-state, high anesthetic-state), and indicia of which state the patient 18 is in can be provided to, and displayed by, and one or more of the displays 20, 26, 56, 66. Also, the anesthetic-state value determined according to equations (1) or (2) may be displayed as a continuum of anesthetic state as a continuum of anesthetic preparedness.

Still other embodiments are within the scope and spirit of the invention and the appended claims. For example, due to the nature of software, functions described above can be implemented using software, hardware, firmware, hard wiring, or combinations of any of these. Features implementing functions may also be physically located at various positions, including being distributed such that portions of functions are implemented at different physical locations. For example, the analyzer 32 may be separate from the monitor 12, e.g., as part of a computer such as a personal computer connected to the monitor 12, the stimulator 14, and the display 20. This separate analyzer may include features such as controlling the stimulus applied by the stimulator 14. Further, the monitor 12 can control the stimulator 14 using control signals and determine stimulus intensity based on the monitor's control signals. Also, any number and/or variety of indications may be provided as to whether the patient 18 is adequately anesthetized (e.g., audible tones, different colors (e.g., red) of visual indicia, flashing visual indicia, etc. Indicating that the patient 18 is not sufficiently anesthetized). The anesthesia supply 16 could include its own display.

What is claimed is:

1. A system for determining anesthetic state of a subject, the system comprising:
    a brain monitor configured to measure at least one parameter of brain activity of the subject and to provide at least one brain monitor output signal indicative of the measured at least one parameter;
    a stimulator configured to apply a non-surgical stimulus perturbation to the subject and to provide at least one stimulus output signal indicative of timing and intensity of non-surgical stimuli applied to the subject;
    an analyzer coupled to the brain monitor and the stimulator and configured to receive the at least one brain monitor output signal and the at least one stimulus output signal, to determine a stimulus difference between the non-surgical stimulus intensity in the absence of the perturbation and in the presence of the perturbation, to determine a monitor difference between the a first value of the at least one parameter in the absence of the perturbation and a second value of the at least one parameter in the presence of the perturbation, to make a comparison of the stimulus difference to determine the anesthetic state and the monitor difference, and to provide an indication of the anesthetic state; and
    a display coupled to the analyzer and configured to receive the indication of the anesthetic state, and in response to receiving the indication of the anesthetic state to provide at least one of an audible sound and a visual image indicative of the indication of the anesthetic state.

2. The system of claim 1 further comprising a housing containing at least the brain monitor and the analyzer.

3. The system of claim 2 wherein the housing further contains at least the display.

4. The system of claim 1 wherein the comparison is a ratio of the stimulus difference and the monitor difference.

5. A monitor for determining anesthetic state of a subject, the monitor being for use with a stimulator for applying a non-surgical perturbation stimulus to a patient and providing indicia of intensity of the applied stimulus, the monitor comprising:
    a sensor adapted to couple to the patient and to sense at least one bodily parameter that is at least partially indicative of anesthetic state, and to provide a sensor output indicative of the sensed at least one bodily parameter;
    an input configured to couple to the stimulator to receive the indicia of timing and intensity of the applied stimulus; and
    an analyzer coupled to the sensor and the input and configured to process the sensor output and the indicia of intensity of the applied stimulus to determine a comparison between (1) the sensor output without the perturbation and the sensor output when the subject responds to the perturbation and (2) the applied stimulus during a time other than when the perturbation is applied and the applied stimulus during application of the perturbation to thereby determine the anesthetic state.

6. The monitor of claim 5 wherein the sensor is configured to sense brain activity.

7. The monitor of claim 5 wherein the comparison is a ratio.

8. A method of determining anesthetic state of a patient prior to performing a procedure on the patient, the method comprising:
    sensing at least one bodily parameter of the patient that is at least partially indicative of anesthetic state;
    providing a sensed signal indicative of the sensed at least one bodily parameter;
    applying a stimulus perturbation to the patient, the stimulus perturbation being different from the procedure;
    analyzing the sensed signal from a first time when the patient is reacting to the stimulus perturbation and from a second time other than the when the patient is reacting to the stimulus perturbation to produce a first analysis result;
    analyzing a first intensity of the stimulus perturbation and a second intensity of a stimulus, if any, provided to the patient during the second time to produce a second analysis result; and
    determining the anesthetic state from the first and second analysis results.

9. The method of claim 8 wherein analyzing the sensed signal includes determining a difference between the sensed signal at the first and second times.

10. The method of claim 9 wherein analyzing the first and second intensities includes determining a difference between the first and second intensities.

11. The method of claim 10 further comprising comparing the difference between the sensed signal and the difference between the first and second intensities.

12. The method of claim 11 wherein the comparing includes determining a ratio of the differences.

13. The method of claim 8 wherein the at least one bodily parameter is indicative of brain activity.

14. The method of claim 8 wherein during the second time no stimulus is applied to the patient.

* * * * *

UNITED STATES PATENT AND TRADEMARK OFFICE
CERTIFICATE OF CORRECTION

PATENT NO. : 6,975,901 B2
DATED : December 13, 2005
INVENTOR(S) : James H. Philip It is certified that error appears in the above-identified patent and that said Letters Patent is hereby corrected as shown below:

<u>Title page,</u>
Item [54], Title, replace "DETERMING" with -- DETERMINING --.

<u>Column 7,</u>
Line 58, after "difference" insert -- and monitor difference --.

<u>Column 8,</u>
Line 26, before "anesthetic" delete "the".

Signed and Sealed this

Twenty-eighth Day of March, 2006

JON W. DUDAS
*Director of the United States Patent and Trademark Office*